US012268833B2

(12) United States Patent
Kulik et al.

(10) Patent No.: US 12,268,833 B2
(45) Date of Patent: Apr. 8, 2025

(54) MICROARRAY RECEPTACLE

(71) Applicant: LTS Lohmann Therapie-Systeme AG, Andernach (DE)

(72) Inventors: Michael Kulik, Urmitz (DE); Thorsten Fehr, Andernach (DE); Stefan Erlhofer, Kempenich (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 817 days.

(21) Appl. No.: 17/423,547

(22) PCT Filed: Nov. 26, 2019

(86) PCT No.: PCT/EP2019/082542
§ 371 (c)(1),
(2) Date: Jul. 16, 2021

(87) PCT Pub. No.: WO2020/148009
PCT Pub. Date: Jul. 23, 2020

(65) Prior Publication Data
US 2022/0072291 A1   Mar. 10, 2022

(30) Foreign Application Priority Data

Jan. 17, 2019   (DE) .......................... 102019200558.6

(51) Int. Cl.
*A61M 37/00*   (2006.01)
(52) U.S. Cl.
CPC . *A61M 37/0015* (2013.01); *A61M 2037/0023* (2013.01)

(58) Field of Classification Search
CPC ...... A61M 37/0015; A61M 2037/0023; A61M 2037/006
See application file for complete search history.

(56) References Cited

U.S. PATENT DOCUMENTS

| 5,817,044 A | 10/1998 | Evers et al. |
| 2002/0091357 A1* | 7/2002 | Trautman .......... A61M 37/0015 606/186 |
| 2008/0183144 A1 | 7/2008 | Trautman et al. |
| 2009/0198189 A1* | 8/2009 | Simons ............. A61M 37/0015 604/173 |
| 2010/0256568 A1 | 10/2010 | Frederickson et al. |

(Continued)

FOREIGN PATENT DOCUMENTS

| CN | 1079916 A | 12/1993 |
| WO | 2008091602 A2 | 7/2008 |
| WO | 2015005143 A1 | 1/2015 |

*Primary Examiner* — James D Ponton
*Assistant Examiner* — Hong-Van N Trinh
(74) *Attorney, Agent, or Firm* — The Webb Law Firm (57) ABSTRACT

A microarray receptacle which has a first side and a second side. Furthermore, the microarray receptacle includes a carrier structure for connecting the microarray receptacle to an application point. To the carrier structure there is connected a carrier surface which in turn is connected to a microarray. An articulation device is arranged between the carrier surface and the carrier structure, the articulation device making possible movement of the microarray connected to the carrier surface relative to the carrier structure along the extent of the microarray. Further, a microarray receptacle cluster with a plurality of such microarray receptacles.

16 Claims, 6 Drawing Sheets

(56) References Cited

U.S. PATENT DOCUMENTS

| | | | |
|---|---|---|---|
| 2011/0276027 A1* | 11/2011 | Trautman | A61M 37/0015 604/173 |
| 2015/0038897 A1* | 2/2015 | Daddona | A61M 37/0015 604/46 |
| 2015/0246214 A1* | 9/2015 | Simmers | A61M 37/0015 604/173 |
| 2015/0258319 A1 | 9/2015 | Simmers | |
| 2015/0290444 A1 | 10/2015 | Wirtanen et al. | |
| 2016/0121092 A1* | 5/2016 | Kato | A61M 37/0015 604/173 |
| 2018/0001071 A1 | 1/2018 | Simmers | |

* cited by examiner

MICROARRAY RECEPTACLE

CROSS-REFERENCE TO RELATED APPLICATIONS

This application is the United States national phase of International Application No. PCT/EP2019/082542 filed Nov. 26, 2019, and claims priority to German Patent Application No. 102019200558.6 filed Jan. 17, 2019, the disclosures of which are hereby incorporated by reference in their entirety.

BACKGROUND OF THE DISCLOSURE

Field of the Disclosure

The invention relates to a microarray receptacle and to a microarray receptacle cluster.

Description of Related Art

Microarrays have a multiplicity of microneedles which usually are arranged on a carrier surface, such as a patch, a plaster or the like, or are connected to a carrier surface. Such microarrays have a high number of microneedles, of for example 500-600 needles per $cm^2$. The needles are of short length, so that when the microneedles are pressed into a patient's skin the needles penetrate only so far into the skin that nerves and blood vessels as far as possible are not contacted by needle tips. The microneedles contain an active ingredient or a medicament. The corresponding active ingredient may be applied to a surface of the needle or be arranged in the needles. It is preferred for the needles to be produced from a material which dissolves in the patient's skin.

When applying microarrays to human skin there is the problem that the introduction of the microneedles into the skin must be reproducible, in order in particular to ensure reliable delivery of medicaments. Also, the introduction of the microneedles must be independent of the user or patient, since otherwise reproducibility would not be guaranteed.

In particular, the introduction of the microneedles should also be independent of the nature of the skin, so that a certain penetration depth is always ensured.

Currently, application of microarrays frequently takes place by a user by hand. Normally, to this end the user removes the microarray from a standard packaging, for example a blister pack. On one hand, the microarray is exposed to contamination from this moment onwards. On the other hand, there is the risk that individual microneedles and/or the entire microarray will be damaged. After removal, the user places the microneedle array on the application site, for example the skin. In the next step, application takes place. To this end, it is common practice for the user for example to press with a finger on the rear side of the microarray and thus apply the needles into the skin. This does not provide reproducible application.

One further problem arises if microarrays with a multiplicity of microneedles or a plurality of microneedle arrays are to be applied to an application point or by the application of a microarray to curved skin surfaces. In this case too, reproducible application currently does not occur.

SUMMARY OF THE DISCLOSURE

The object of the invention is to create a microarray receptacle which improves the reproducibility of the application of microarrays. One further object of the invention consists in providing a microarray receptacle cluster for optimized application of a plurality of microarrays.

This object is achieved according to the invention by a microarray receptacle having the features of claim 1 and by a microarray receptacle cluster having the features of claim 15.

The microarray receptacle according to the invention is preferably a microarray receptacle for storage and/or handling and/or guidance in applying a microarray. The microarray receptacle has a first side, the first side preferably being the upper side of the microarray receptacle. This first side is in particular the side facing away from the application point, in particular the skin. Furthermore, the microarray receptacle has a second side, preferably a lower side, this side being in particular the side facing towards the skin. The microarray receptacle has a carrier structure which is formed to be connected to an application point. The application point is particularly preferably the skin of a user. The carrier structure thus preferably has the contact surface of the microarray receptacle with the skin. This contact surface may be made in particular adhesive. Thus the microarray receptacle can be glued on the skin with the contact surface of the carrier structure. Further still, the microarray receptacle has a carrier surface connected to the carrier structure. In a preferred embodiment, this carrier surface is formed as an in particular round or rectangular plate. It is preferred to embody the carrier surface with a substantially two-dimensional surface. A microarray is connected to the carrier surface. The connection between the microarray and carrier surface may take place in particular such that a patch of the microarray is glued and/or welded to the carrier surface. On the other hand, a configuration in which the microarray is formed in one piece, also referred to as "integrally", with the carrier surface is also possible. It is possible for the microstructures, preferably the microneedles of the microarray, to be attached directly to the carrier surface. It is preferred for the carrier structure to be formed and/or connected to the carrier surface such that in the initial state there is a distance between the carrier surface and the microarray from the application point. The carrier surface may be formed such that it represents a sterile barrier, in particular towards the first side. Further still, the microarray receptacle has an articulation device between the carrier surface and carrier structure. The articulation device is formed such that it makes possible movement of the microarray connected to the carrier surface relative to the carrier structure. This relative movement of the microarray relative to the carrier structure takes place in particular such that the movement takes place along the extent of the microstructures, preferably in the case of microneedles, of the microarray. In other words, the microarray on the carrier surface is connected mounted with the carrier structure by way of the articulation device such that in particular the distance of the microarray from the skin is overcome by way of the movement and thus application of the microarray into the skin takes place. The articulation device in this case is in particular formed such that it makes possible merely a movement along the extent of the microstructures. However, a configuration is also possible in which additional movements, such as in particular tilting or transverse movements, are possible. The articulation device can be embodied such that it permits merely movement on one side, in particular towards the skin. On the other hand, the articulation device may also be embodied such that it permits a movement on both sides, in particular a back-and-forth movement. The carrier structure preferably forms an in particular cylindrical housing of the microarray receptacle. The cylindrical shape of the housing may preferably have a circular or rectangular, in particular square, or oval base.

In a preferred embodiment, the articulation device has at least a first flexure. Preferably the first flexure is formed in one piece with the carrier surface. If a one-piece configuration consisting of the flexure and carrier surface is present, it is in particular possible for the microarray to be connected directly to the flexure. In this case, a one-piece configuration of the microarray and flexure is also possible.

Preferably the articulation device has a second flexure in addition to the first flexure. In this case, it is preferred for the first flexure and the second flexure to be arranged substantially parallel to each other. The second flexure forms in particular an action surface for preferably external actions on the microarray receptacle. In particular, the second flexure may be formed such that it can be moved from the outside. It is preferred for the second flexure which is thus moved to be able to act on the first flexure. The two flexures are in particular formed or arranged such that the microarray and/or the carrier surface can undergo merely a one-dimensional, preferably linear, deflection. Preferably this deflection is a deflection along the extent of the microstructures of the microarray. Preferably a spacer is provided between the first flexure and the second flexure.

In a preferred embodiment, the microarray receptacle has a blocking device for fixing the first flexure and the second flexure relative to each other. In particular, the blocking device is an engagement device which upon engagement prevents a relative movement of the first flexure relative to the second flexure. Alternatively or additionally, it is possible for the engagement device upon engagement to prevent a relative movement between the first flexure and the carrier structure. It is preferred for the engagement device to be formed such that upon engagement it prevents a relative movement between the first flexure, second flexure and carrier structure. Preferably the engagement device is an engagement pin between the first flexure and the second flexure. The engagement pin may be configured such that in the initial state it is already connected to the first or the second flexure and upon engagement engages with the respective other flexure and thus prevents relative movement of the two flexures. On the other hand, it is also possible for the engagement pin upon engagement to engage with both flexures. Likewise it is possible for the engagement pin furthermore to engage with the carrier structure.

The first flexure and/or the second flexure is/are in particular a linear flexure. More preferably, it is a linear plate-type flexure. A linear plate-type flexure is a rigid plate with at least two regions connected in a movable manner relative to each other by way of lands. The mobility of the regions relative to each other is limited in particular to parallel and/or right-angled movements. The lands and/or the regions are produced in particular by means of stamping and/or laser-cutting a rigid plate. A linear plate-type flexure is also referred to as a "diaphragm flexure". It is preferred for the carrier surface to be configured in one piece with the articulation device and/or with the microarray. It is also possible for the carrier surface to be connected in one piece with the carrier structure.

In a preferred embodiment, the articulation device has a degree of freedom of 1. Preferably the articulation device thus permits merely linear deflections, in particular along the extent of the microstructures of the microarray. In other words, the articulation device is preferably configured such that it merely makes movements in the Z-direction possible. It is particularly preferred for the articulation device to permit merely movements in one direction, preferably in the needle-tip direction of the microneedles.

Preferably the microarray receptacle has a guidance device for in particular linear guidance of the carrier surface. The guidance device is preferably embodied to guide the articulation device. In particular, the guidance device is arranged between the first flexure and the second flexure. The guidance device preferably has an in particular round guide rod. Preferably the guide rod guides the first flexure and/or the second flexure, the first flexure and/or the second flexure preferably having openings for guidance by means of the guide rod.

On one hand, it is possible for the articulation device to be configured such that it independently moves the carrier surface back into the starting position after deflection. On the other hand, it is possible for the articulation device to hold the carrier surface in the deflected position. According to this first possible configuration, thus in particular upon penetration of the microneedles into the skin subsequent withdrawal of the microneedles from the skin takes place as soon as the articulation device is no longer deflected, in particular from outside. According to the possible second configuration, it is in particular possible that, after deflection of the articulation device for the first time, the microneedles penetrate into the skin and preferably are deflected by the articulation device and thus held penetrated into the skin. To this end, it is preferred for the microarray receptacle to have a fixing device, in particular an engagement fixing device, the fixing device blocking or fixing the articulation device and/or the carrier surface in the deflected position, and in such a manner, at least temporarily, preventing movement of the microarray back into the starting position. In particular, the engagement fixing device is an engagement hinge which bears the articulation device, and/or a snap fastener which acts in particular between the carrier surface and carrier structure. It is preferred for the microarray receptacle, in particular the articulation device, to have a pre-tensioning device, such as a spring. The pre-tensioning device is in particular embodied such that it triggers acceleration of the carrier surface during the deflection and/or holding of the carrier surface in the deflected position.

It is preferred for the microarray receptacle to have a force introduction structure connected indirectly or directly to the rear side of the microarray.

In particular, the force introduction structure may be connected to the carrier surface opposite the microarray. It is preferred for the force introduction structure to be configured convexly.

The microarray receptacle has in particular a base film. The base film is preferably arranged on the second side of the microarray receptacle. In a preferred embodiment, the base film represents a sterile barrier of the microarray on the second side towards the surroundings. It is possible for the base film to be configured such that it can be penetrated by the microarray. Thus in particular microneedles of the microarray can pierce the base film.

It is preferred for the base film to be connected to the carrier structure. It is particularly preferred in this case for the base film to be connected to the carrier structure in a peelable or detachable manner. This peelable connection takes place in particular by gluing the base film to the carrier structure. Thus it is possible, in particular prior to use, for a user to detach the base film from the carrier structure and in such a manner to reveal the microarray.

It is possible for the base film to have an adhesive layer. In such a manner, it is possible in particular to fasten the microarray receptacle to an application point.

The microarray receptacle preferably has a cover film. The cover film is connected in particular to the carrier structure. In this case a fixed, non-detachable connection is preferred. In particular, the cover film may be welded, preferably by ultrasonic welding, or bonded to the carrier structure. The cover film preferably forms a sterile barrier on the first side of the microarray receptacle towards the surroundings.

The cover film is made in particular flexible and/or fragile. In the case of a flexible configuration, in particular an action taking place from outside on the cover film may take place, so that the cover film yields flexibly. In the case of a fragile, preferably perforated, configuration, the cover film can tear upon an external action and thus permit action on the microarray receptacle from the outside.

In a preferred configuration, the microarray receptacle has a connection device. The connection device is provided in particular on the first side of the microarray receptacle. It is particularly preferred for the connection device to be connected to the carrier structure, preferably in one piece. The connection device is in particular a connection device for a microarray applicator. The connection device preferably has a thread and/or a plug-type connector and/or a form-fit connecting piece and/or a gluing point and/or a flange and/or a bayonet-fastener connecting piece and/or a magnetic connecting piece, in particular a magnet.

The microarray receptacle cluster according to the invention has a plurality of microarray receptacles according to the invention in accordance with the above definition. The plurality of microarray receptacles may have identical or different microarrays, so that in particular different microarrays, with different active substances and/or different needle numbers, etc. may be present. The carrier surfaces and/or the base films and/or the cover films and/or the carrier structures of the plurality of microarray receptacles are preferably connected together, in particular a one-piece connection being preferred. In such a manner, a plurality of microarray receptacles can be connected together. In particular, in such a manner a plurality of microarray receptacles can be jointly, preferably continuously, produced. It is also advantageously possible in such a manner to apply a plurality of microarray receptacles connected together jointly to a body site which is to be applied, in particular a curved skin part. This plurality of microarray receptacles can then be applied simultaneously or in a chronologically staggered manner.

BRIEF DESCRIPTION OF THE DRAWINGS

The invention will be discussed in greater detail below using a preferred embodiment with reference to the drawings.

Therein.

Similar or identical components or elements are identified with the same reference numerals in the drawings. In particular for improved clarity, preferably already-identified elements are not provided with reference numerals in all the figures.

DETAILED DESCRIPTION

Figure 1:
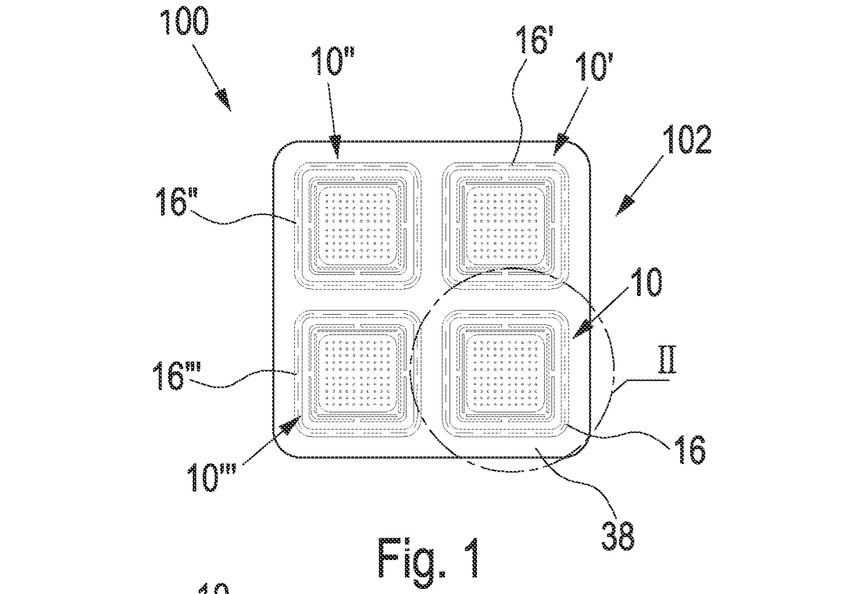
FIG. 1 is a schematic plan view of a microarray receptacle cluster according to the invention.

FIG. 1 shows a plan view of the lower side of an embodiment of a microarray receptacle cluster 100 according to the invention (with base film 36 removed).

The microarray receptacle cluster 100 shows a plurality of embodiments of microarray receptacles 10, 10', 10", 10''' according to the invention which are connected together by way of a cover film 38. To apply the microarray receptacle cluster, the same is placed in particular on human skin, so that the side 102 illustrated of the microarray receptacle cluster 100 lies on the skin and thus is shielded towards the surroundings by the cover film 38. The cover film 38 and/or the microarray receptacles 10, 10', 10", 10''' in this case are preferably configured to be flexible, so that the microarray receptacle cluster 100 adapts in particular to a curved portion of skin.

Once the microarray receptacle cluster 100 has been placed on the skin, in particular individual microarray receptacles 10 can be applied independently of each other or it is possible to apply all the microarray receptacles jointly.

Instead of the embodiment illustrated, it is possible for the carrier structures 16, 16', 16", 16''' to be connected together, in particular in one piece.

Figure 2:
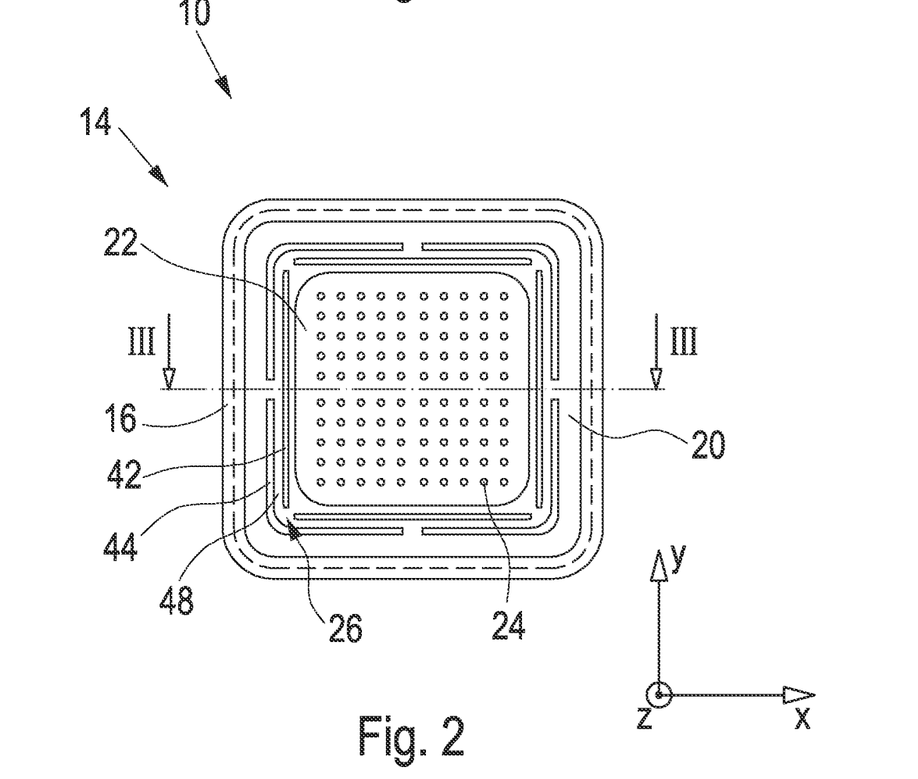
FIG. 2 is a detail view of the region II of FIG. 1, which shows an embodiment of a microarray receptacle according to the invention.

FIG. 2 shows a detail view of the microarray receptacle 10 of FIG. 1. FIG. 2 shows the lower side 14 of the microarray receptacle 10, which is located opposite the upper side 12, which cannot be seen in this view.

Figure 3:
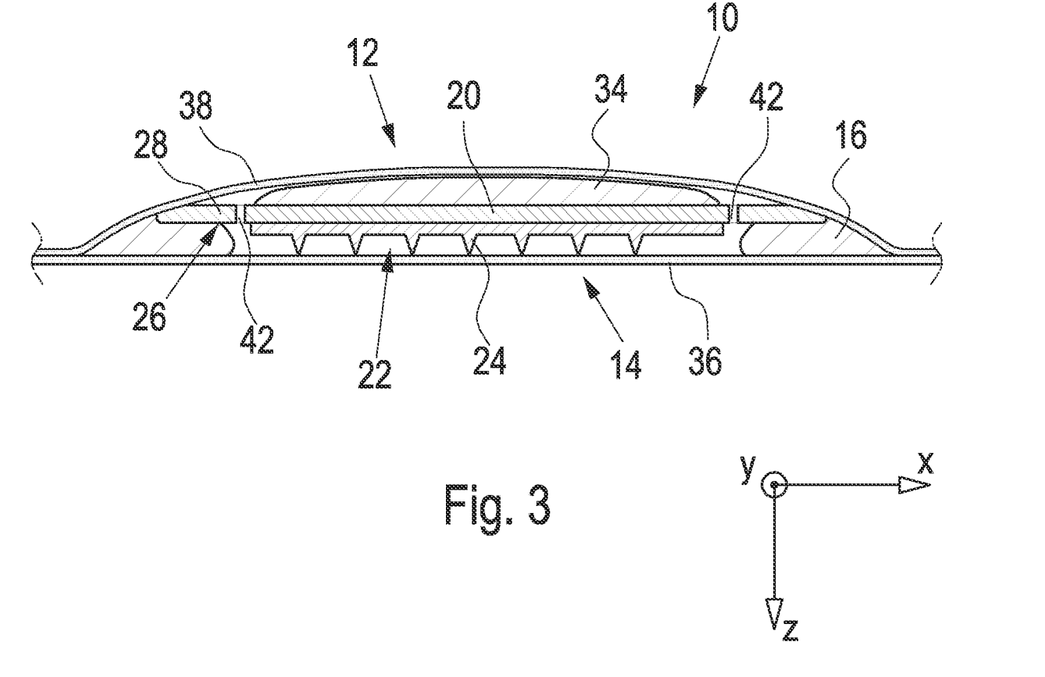
FIG. 3 is a schematic sectional view of an embodiment of a microarray receptacle according to the invention, the microarray receptacle corresponding substantially to the microarray receptacle of FIG. 2 along section plane III.

The microarray receptacle 10 has an encircling carrier structure 16 which partly projects beyond a carrier surface 20, the carrier structure 16 being connected to the carrier surface 20 by the region which overlaps with the carrier surface 20 (see FIG. 3). Preferably the projecting region of the carrier structure 16 is connected to the cover film 38 which is not illustrated in FIG. 2 (see FIGS. 1 and 3). The connection between the cover film 38 and carrier structure 16 is preferably embodied by means of welding and/or gluing, a one-piece or other configuration however also being possible. The connection between the carrier structure 16 and carrier surface 20 may be made in particular by means of gluing and/or welding, but also be configured in one piece. The carrier surface 20 is connected to a microarray 22 with a plurality of microneedles 24. The microarray 22 as illustrated is a patch with microneedles 24 arranged thereon, which are in particular formed in one piece therewith. The microneedles 24 in this case run preferably conically out of the image plane (in the Z-direction). Instead of the embodiment illustrated, it is also possible to connect the microarray 22 directly to the carrier surface 20, a one-piece connection also being possible. Accordingly, it is possible to configure the carrier surface 20 in one piece with the microarray 22 and/or the microneedles. The carrier structure 16 preferably has a height (projecting out of the image plane in the illustration) which ensures in particular a distance between the carrier surface 20 and an application point.

The microarray receptacle 10 of FIG. 2 furthermore has an articulation device 26. The articulation device 26 in this case is embodied as a flexure, in particular as a linear plate-type flexure. To this end, the carrier structure 16 has slits 42, 44 which are produced in particular by means of punching a plate which preferably corresponds substantially to the carrier surface 20. Between these slits 42, 44 there are lands 48. These lands 48, which are preferably made flexible, permit mobility of the inner region of the carrier surface 20 relative to the outer region. The articulation device 26 makes in particular movement of the microarray in the Z-direction possible. Owing to its being embodied in the embodiment of the flexure articulation device 26 illustrated, however, tilting of the microarray 22 is also possible, so that movement about the X-axis and/or Y-axis is likewise possible.

It is possible for the microarray receptacles 10 to be formed independently of the microarray receptacle cluster 100. Accordingly, the microarray receptacles 10 according to the embodiment of FIG. 2 would have in particular a separate cover film 38.

FIG. 3 shows a sectional view of an embodiment of a microarray receptacle 10 according to the invention, the microarray receptacle 10 corresponding substantially to the microarray receptacle of FIG. 2 (independently of the microarray receptacle cluster 100) along section plane III.

Unlike the embodiment of FIG. 2, in FIG. 3 a base film 36 is illustrated. This base film 36 is connected to the carrier structure 16. This connection between the base film 36 and carrier structure 16 is preferably embodied as an adhesive one. It is particularly preferred for the base film 36 to be made peelable or removable, so that in particular prior to application a user can remove the base film 36 from the microarray receptacle 10. Alternatively or additionally, it is possible for the base film 36 to be embodied such that it can be pierced by the microarray 22, i.e. in particular the microneedles 24. In particular, the base film 36 may have, preferably on the lower side illustrated, an adhesive layer, so that the microarray receptacle 10 can be connected to an application point in adhesive manner by way of the adhesive layer of the base film 36.

In the form illustrated, the microarray receptacle 10 is in the non-deflected or non-applied position. The flexure 26, which is in particular a linear plate-type flexure, accordingly is not deflected. To the rear side of the microarray 22 or the rear side of the carrier surface 20 there is connected a convex force introduction structure 34. This convex force introduction structure 34 makes it possible, in particular in the case of an introduction of force by means of an oppositely convex applicator, for the application of the microarray 22 to take place at a normal vector to the application point, i.e. in particular to the skin. Thus as a result deflection along the Z-axis is brought about and optimum puncturing and application of the microneedles into the skin is possible.

The microarray 22 is protected from the surroundings by way of the base film 36 and also the cover film 38 and/or the carrier surface 20. In this case, in particular sterile protection from the surroundings is possible.

Figure 4:
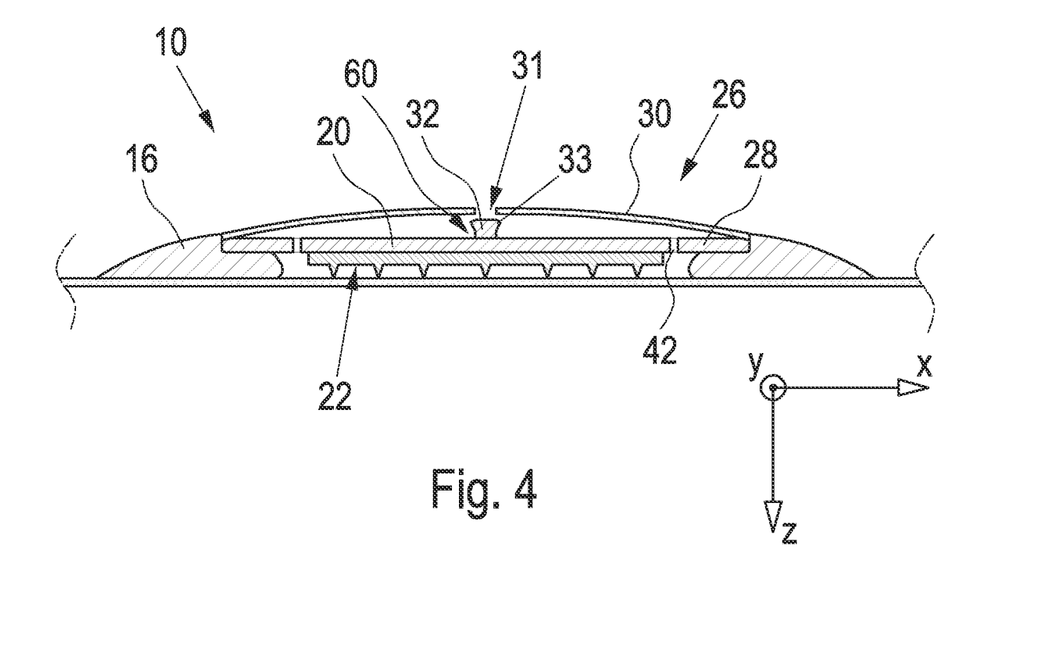
FIG. 4 is a schematic sectional view of a further embodiment of a microarray receptacle according to the invention.

FIG. 4 shows a further embodiment of a microarray receptacle 10 according to the invention. The embodiment of FIG. 4 for the most part corresponds to the embodiment of FIG. 3. In contrast to the embodiment of FIG. 3, the microarray receptacle of FIG. 4 does not have a force introduction structure 34. Likewise, no cover film 38 is illustrated in the embodiment of FIG. 4. However, it is likewise possible to provide a cover film 38 in the embodiment of FIG. 4.

Furthermore, the embodiment of the articulation device 26 of FIG. 4 differs from the embodiment of FIG. 3. The articulation device 26 in this case has a first flexure 28, this flexure 28 corresponding substantially to the embodiment of FIG. 3, i.e. being embodied in particular as a linear plate-type flexure. Furthermore, the microarray receptacle has a second flexure 30 above the first flexure 28. The second flexure 30 is preferably a plate, consisting in particular of spring steel, which is curved upwards and in such a manner is in the pre-tensioned state. In other words, the embodiment of the second flexure 30 corresponds to an embodiment in the manner of a "clicker". When pressure is applied on the second flexure 30 from above, it is deformed and flips onto the opposite side, whereupon the second flexure 30 curves downwards and remains in this position. Because of this change in deformation, the second flexure 30 acts on the first flexure 28 and likewise deflects it. As a result, deflection or application of the microarray 22 connected to the first flexure takes place.

In the embodiment illustrated, the microarray receptacle 10 has an engagement device 60. As illustrated, the engagement device 60 has a pin 32 and an opening 31 in the second flexure 30. The pin 32 is connected to the first flexure 28, in particular formed in one piece therewith. Preferably the pin 32 has approximately a half-bone-shaped structure, so that a sort of hemisphere or thickened portion 33 is provided at one end. The pin 32 tapers towards the other side, which is connected to the first flexure 28. Upon deflection of the second flexure 30, the second flexure 30, by means of an opening 31 which is provided, is pushed over the thickened portion 33 of the pin 32, which is in particular made flexible. As a result, engagement of the second flexure 30 with the first flexure 28 takes place, so that subsequent relative movement is prevented between the flexures 28, 30. In other words, the second flexure 30 is engaged with the first flexure 28. Because of the pre-tensioning of the second flexure 30, the first flexure 28 and the second flexure 30 remain in the deflected position, so that the microarray 22 is deflected and thus kept applied.

Instead of the embodiment with engagement device 60 illustrated here, an embodiment of the microarray receptacle 10 without an engagement device and accordingly preferably also without an opening 31 in the second flexure 30 is likewise possible.

Because of the provision of the two flexures 28, 30, associated preferably parallel to each other, in particular in contrast to the embodiment of FIG. 3 no tilting, i.e. no movement, of the microarray 22 about the X-axis and/or Y-axis is possible. The two flexures 28, 30 arranged relative to each other in such a manner ensure that merely deflection along the Z-axis is possible.

Figure 5:
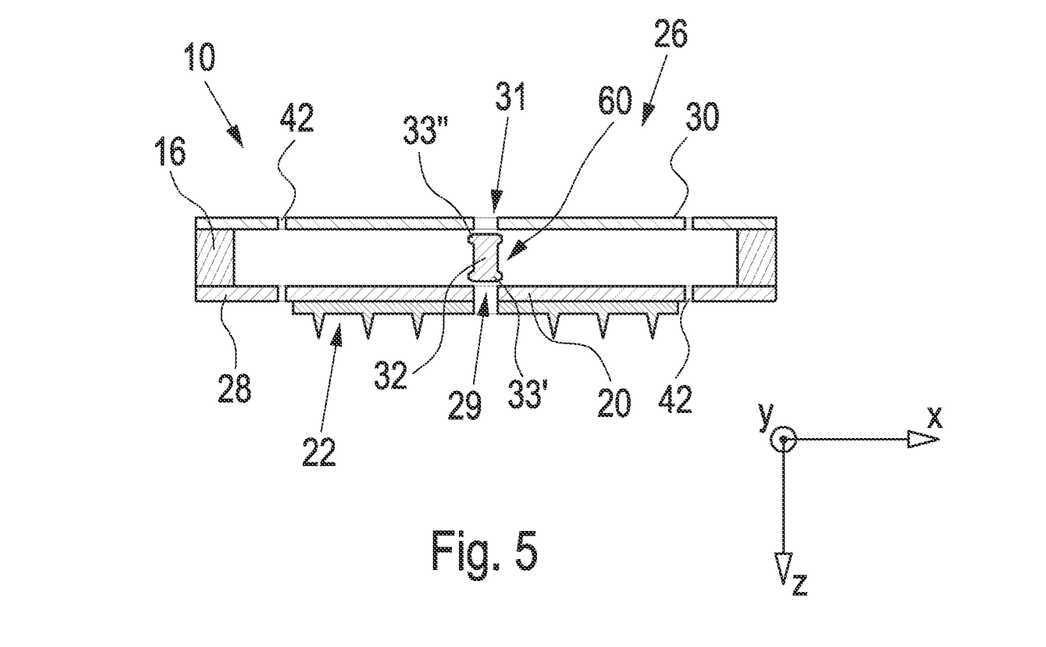
FIG. 5 is a schematic sectional view of a further embodiment of a microarray receptacle according to the invention.

FIG. 5 shows a further embodiment of a microarray receptacle 10 according to the invention. The microarray receptacle 10 has two flexures 28, 30. The two flexures 28, 30 in this case are embodied in the manner of the flexure 28 of FIG. 3, i.e. embodied in particular as linear plate-type flexures. Again, the composition of the two flexures 28, 30 ensures that merely deflection along the Z-axis is possible.

The first flexure 28 has an opening 29 and the second flexure 30 has an opening 31. Between the openings there is provided an engagement device 60 which in the embodiment illustrated is embodied as an engagement pin 32. The engagement pin 32 is substantially bone-shaped, so that thickened portions 33', 33" are located at the two ends of the engagement pin 32. Upon deflection of the second flexure 30 in the positive Z-direction, likewise deflection of the first flexure 28 and thus application of the microarray 22 in the Z-direction takes place owing to the action of the second flexure 30 on the first flexure 28. Furthermore, this deflection ensures that the first flexure 28 and the second flexure 30 with the openings 29, 31 push over the engagement pin 32 and remain engaged in the middle region of the engagement pin 32. In such a manner, engagement of the first flexure 28 relative to the second flexure 30 takes place.

Between the first flexure 28 and the second flexure 30 there is provided a carrier structure 16. In the manner of the embodiment of FIG. 3, this carrier structure 16 can likewise extend below the first flexure 28 and in such a manner produce in particular a distance from the application point. Furthermore, in the embodiment of FIG. 5, in the manner of the embodiment of FIG. 3, likewise the provision of a base film 36 and/or cover film 38 and/or a force introduction structure 34 can be implemented.

Figure 6A:
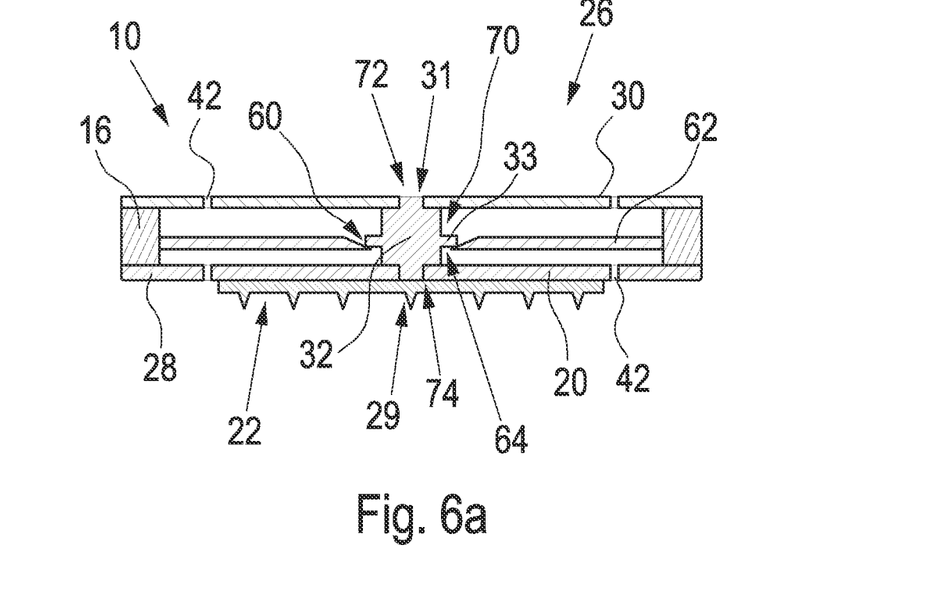
FIG. 6a is a schematic sectional view of a further embodiment of a microarray receptacle according to the invention in the starting position.

FIG. 6a shows a further embodiment of a microarray receptacle 10 according to the invention. The embodiment is based on the embodiment of FIG. 5.

In contrast to the embodiment of FIG. 5, the pin 32 in the initial state is already inserted into the openings 29, 31. The pin 32 in this case corresponds approximately to the embodiment of a shaft with two shaft steps 72, 74, very widely-varying forms of the pin 32, for example round, rectangular, square, etc., being possible. Shaft step 72 is inserted into opening 31, and shaft step 74 into opening 29. The pin 32 in this case functions on one hand as a spacer between the first flexure 28 and the second flexure 30. Further still, the embodiment has a guidance device 70 which encompasses the shaft steps 72, 74 of the pin 32 and the openings 29, 31. The pin 32 in this case as a type of guide rod ensures linear guidance of the first flexure 28 and the second flexure 30, so that merely deflection in the Z-direction is possible. If accordingly such an action takes place on the first flexure 28 that it would experience tilting or a torque, the pin 32 absorbs this torque and prevents the tilting. Consequently, merely linear deflection of the microarray 22 in the Z-direction takes place.

Figure 6B:
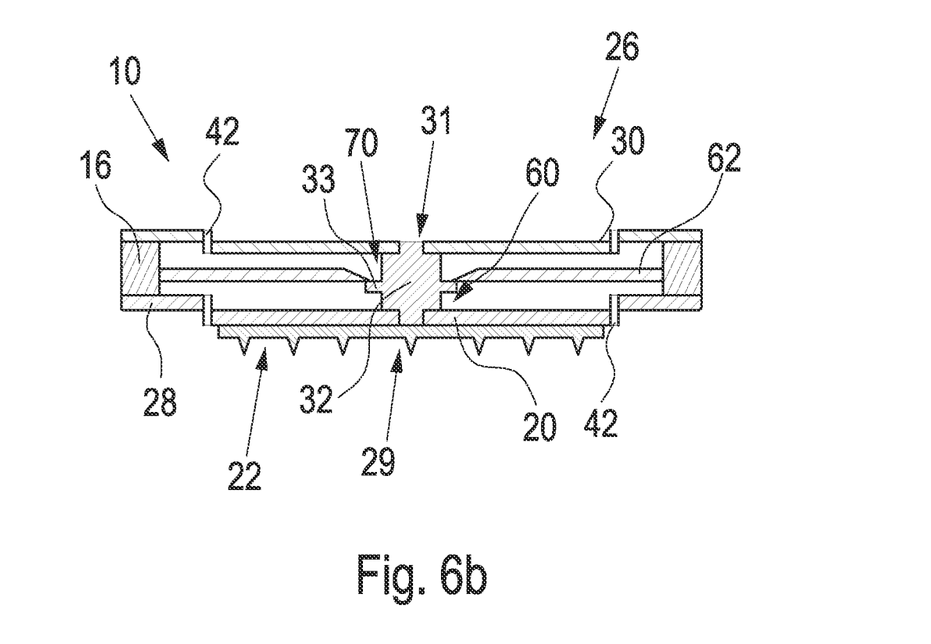
FIG. 6b is a schematic sectional view of the microarray receptacle of FIG. 6a in the applied position.

Likewise, the embodiment has an engagement device 60. The engagement device 60 comprises the protrusion 33 of the pin 32 and the engagement plate 62. The engagement plate 62 is illustrated connected immovably to the carrier structure 16, in particular configured in one piece, and has an opening 64 provided with an incline. In the starting position (FIG. 6a), the protrusion 33, which may also be formed as a bead, lies against the opening 64 of the engagement plate 62. Upon deflection (FIG. 6b) of the second flexure 30, for example because of pressure on the same by a user, in the Z-direction, a transfer of force onto the first flexure 28 takes place by way of the pin 32, and thus likewise deflection of the pin 32 and also the first flexure 28 in the Z-direction. In this case the protrusion 33 overcomes the opening 64 of the engagement plate 62. As a result, the pin 32 engages below the engagement plate 62 (in the Z-direction). This results in fixing of the first flexure 28 in the deflected position, as a result of which a type of subsequent pressing of the microarray 22 connected to the first flexure 28 occurs. Thus it is possible to keep the microarray 22 applied. In particular, owing to the incline of the opening 64, once the protrusion 33 has passed through the opening 64 subsequent passing-through in the opposite direction and thus a return into the starting position is prevented.

It is possible for the second flexure 30 after initial deflection to move back into the starting position again. This can be brought about in particular in that the plug-type connection between the shaft step 72 and opening 31 is made detachable. On the other hand, it is possible for shaft step 72 with opening 31 and/or shaft step 74 with opening 29 to be configured non-detachably, in particular in one piece. Likewise, it is possible for pin 32 not to have any shaft steps 72, 74 and/or for the flexures 28, 30 not to have any openings 29, 31, but for pin 32 to be connected directly on one side to the first flexure 28 and on the other side to the second flexure 30, preferably non-detachably, in particular configured in one piece.

The protrusion 33 may be configured to be flexible. Alternatively or additionally, the engagement plate 62 or the region of the opening 62 of the engagement plate 62 may be configured to be flexible.

An embodiment in the manner of the embodiment of FIG. 6a which does not have an engagement device 60, i.e. in particular does not have an engagement plate 62 and/or a protrusion 33 on pin 32, is also possible.

Figure 7:
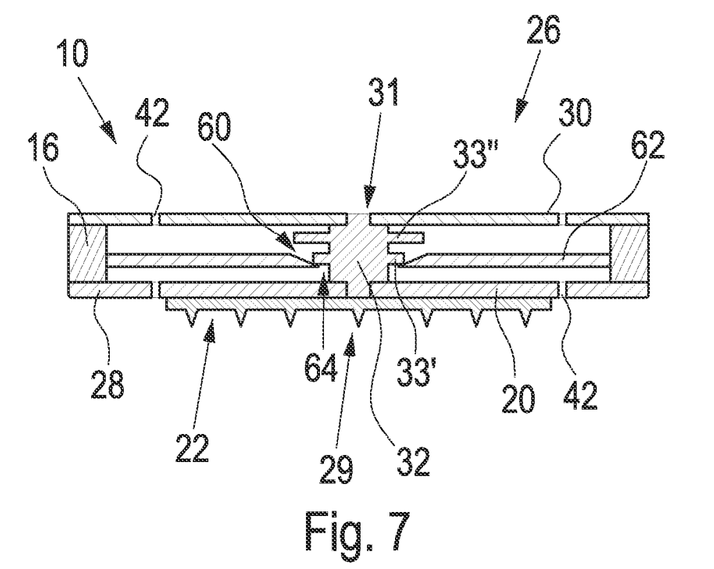
FIG. 7 is a schematic sectional view of a further embodiment of a microarray receptacle according to the invention.

FIG. 7 shows a further embodiment of a microarray receptacle 10 according to the invention. The embodiment corresponds substantially to the embodiment of FIG. 6a.

Unlike the embodiment of FIG. 6a, the engagement device 60 of this embodiment has in addition to the protrusion 33' a further protrusion 33" which is made wider than the protrusion 33'. Once the protrusion 33' has passed through the opening 64, by means of protrusion 33' and protrusion 33" engagement of the pin in the opening 64 on the engagement plate 62 on both sides occurs. Because of the width of the protrusion 33" which lies against the engagement plate 62, further deflection in the Z-direction is prevented. Preferably in such a manner after deflection for the first time permanent engagement and hence blocking of the microarray receptacle occurs.

Figure 8A:
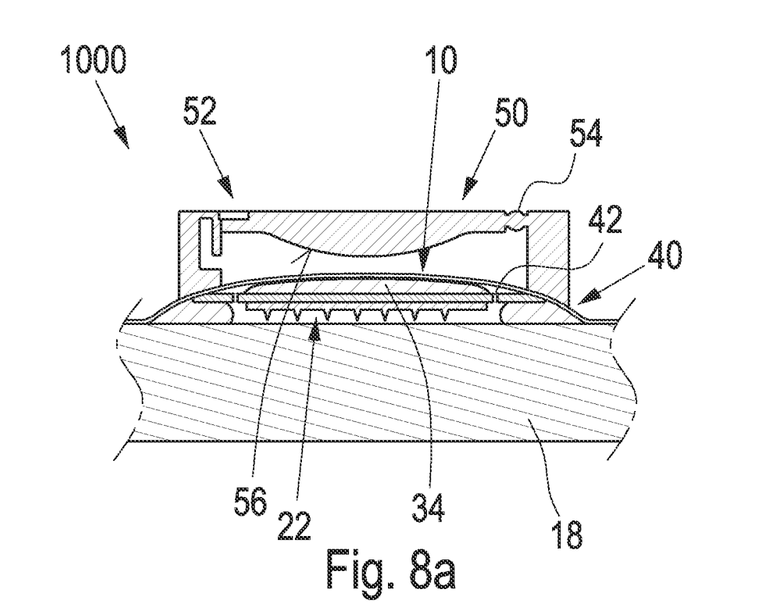
FIG. 8a is a schematic sectional view of an application system with a microarray applicator and an embodiment of a microarray receptacle according to the invention in the starting position.

FIG. 8a shows the microarray receptacle 10 of FIG. 3 arranged on an application point 18, the application point 18 being in particular the skin of a user or patient. The base film 36 has been pulled off or removed for application.

A substantially cuboidal-cylindrical microarray applicator 50 has been placed on the microarray receptacle 10 or connected to the microarray receptacle 10. In addition to the cuboid form, which may for example be square or rectangular, further forms, such as a regular-cylinder form, etc. are possible. The connection of the microarray receptacle 10 to the microarray applicator 50 takes place in particular at a connection device 40 of the microarray receptacle 10, this preferably being configured as a thread and/or engagement device and/or form-fit connecting piece or flange, the microarray applicator having a corresponding mating connecting piece. In this case, in particular microarray receptacle 10 has one or more such connection devices 40 and the microarray applicator 50 has corresponding mating pieces for this in order to produce an in particular severable connection.

The microarray applicator 50 has an articulation 54 on one side and a predetermined breaking point 52 on the other side. Likewise, the microarray applicator has a convex structure 56 which is made oppositely convex to the force introduction structure 34 of the microarray receptacle 10.

The microarray receptacle 10 and microarray applicator 50 connected thereto jointly represent an application system 1000.

Figure 8B:
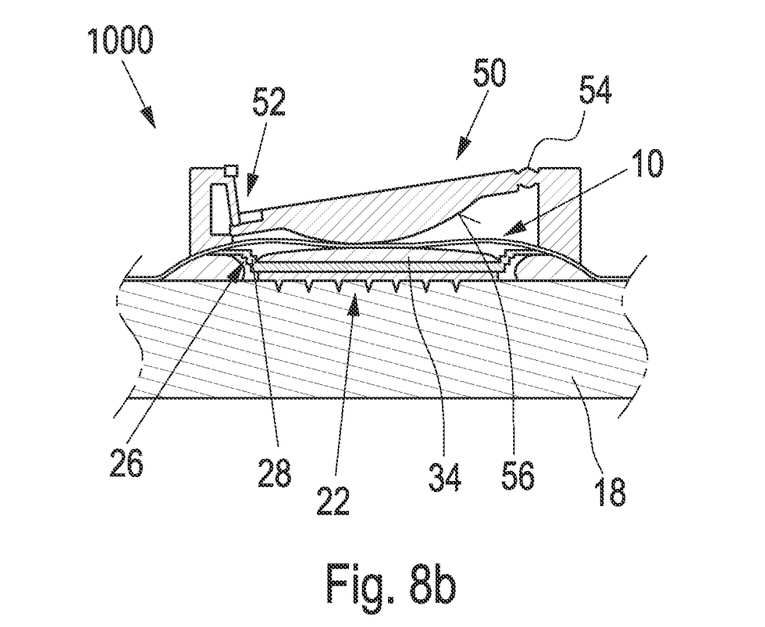
FIG. 8b is a schematic sectional view of the device of FIG. 7a in the applied position.

FIG. 8b shows the application system 1000 of FIG. 8a in the applied position.

For example, because of a user pressing on the illustrated upper side of the microarray applicator 50, breaking occurred at the predetermined breaking point 52, so that deflection of the convex structure 56 of the microarray applicator 50 about the articulation 54 occurs. The breaking of the predetermined breaking point takes place in particular if a desired load is applied, the desired load preferably corresponding to an optimum application force of the microarray. In the deflected position, the convex structure 56 acts on the force introduction structure 34 of the microarray receptacle. Because of the opposing convex structures, a concentrated load between the structures 56, 34 occurs and application along the normal vector to the skin takes place. In this case, the flexure 28 with microarray 22 connected thereto is pushed into the application point 18 around the articulation device 26. It is particularly preferred for the predetermined breaking point 52 to be embodied such that it breaks upon a predefined impulse, this impulse corresponding in particular to an optimum application force for the microarray 22.

Preferably, the microarray applicator 50 has an engagement mechanism which fixes the convex structure 56 engaged in the deflected position. In such a manner, a type of subsequent pressing of the convex structure 56 onto the force introduction structure 34 of the microarray receptacle is provided. This means that in particular lasting application is possible.

Instead of triggering or applying the microarray receptacle 10 with microarray applicator 50, other types of triggering are also possible. Preferably, the microarray receptacle 10 can take place by hand, in particular with a finger of a user. Other microarray applicators can also be used.

The invention claimed is:

1. A microarray receptacle comprising:
   a first side;
   a second side;
   a carrier structure for connecting the microarray receptacle to an application point;
   a carrier surface connected to the carrier structure;
   a microarray connected to the carrier surface; and
   an articulation device between the carrier surface and the carrier structure,
   wherein the articulation device makes possible movement of the microarray connected to the carrier surface relative to the carrier structure along an extent of the microarray,
   wherein the articulation device comprises at least a first flexure and a second flexure such that the first flexure and the second flexure permit only a linear deflection of the microarray,
   wherein the first flexure is formed in one piece with the carrier surface,
   wherein the first flexure and the second flexure are arranged substantially parallel to each other, and
   wherein the microarray receptacle further comprises an engagement device between the first flexure and the second flexure, so that upon engagement of the engagement device a relative movement between the first and second flexures and the carrier structure is prevented.

2. The microarray receptacle according to claim 1, wherein the first flexure and/or the second flexure are linear plate-type flexures.

3. The microarray receptacle according to claim 1, wherein the carrier surface is formed in one piece with the articulation device and/or with the microarray.

4. The microarray receptacle according to claim 1, wherein the articulation device has a degree of freedom of 1.

5. The microarray receptacle according to claim 1, wherein the articulation device is formed such that after deflection it independently returns into a starting position, or is formed such that after deflection it remains in a deflected position.

6. The microarray receptacle according to claim 1, further comprising a base film which can be penetrated by the microarray, wherein the base film closes off, in a sterile manner, the microarray receptacle towards the surroundings on the second side.

7. The microarray receptacle according to claim 6, wherein the base film is connected to the carrier structure.

8. The microarray receptacle according to claim 1, further comprising a cover film connected to the carrier structure, wherein the cover film closes off, in a sterile manner, the microarray receptacle towards the surroundings on the first side.

9. The microarray receptacle according to claim 8, wherein the cover film is flexible and/or fragile.

10. The microarray receptacle according to claim 1, wherein the microarray receptacle, on the first side, comprises a connection device for connecting to a microarray applicator, wherein the connection device comprises a thread and/or an engagement device and/or a form-fit connecting piece and/or a flange.

11. A microarray receptacle cluster comprising a plurality of microarray receptacles according to claim 1, wherein the carrier surfaces of the plurality of microarray receptacles, and/or base films of the plurality of microarray receptacles, and/or cover films of the plurality of microarray receptacles, and/or the carrier structures of the plurality of microarray receptacles are connected together in one piece.

12. A microarray receptacle comprising:
   a first side;
   a second side;
   a carrier structure for connecting the microarray receptacle to an application point;
   a carrier surface connected to the carrier structure;
   a microarray connected to the carrier surface; and
   an articulation device between the carrier surface and the carrier structure,
   wherein the articulation device makes possible movement of the microarray connected to the carrier surface relative to the carrier structure along an extent of the microarray,
   wherein the articulation device comprises at least a first flexure and a second flexure such that the first flexure and the second flexure permit only a linear deflection of the microarray,
   wherein the microarray receptacle further comprises a guidance device between the first flexure and the second flexure, and
   wherein the guidance device comprises a guide rod.

13. The microarray receptacle according to claim 12, wherein the first flexure is formed in one piece with the carrier surface.

14. The microarray receptacle according to claim 13, wherein the first flexure and the second flexure are arranged substantially parallel to each other.

15. The microarray receptacle according to claim 14, further comprising an engagement device between the first flexure and the second flexure, so that upon engagement of the engagement device a relative movement between the first and second flexures and the carrier structure is prevented.

16. A microarray receptacle comprising:
- a first side;
- a second side;
- a carrier structure for connecting the microarray receptacle to an application point;
- a carrier surface connected to the carrier structure;
- a microarray connected to the carrier surface; and
- an articulation device between the carrier surface and the carrier structure,
- wherein the articulation device makes possible movement of the microarray connected to the carrier surface relative to the carrier structure along an extent of the microarray,
- wherein the articulation device comprises at least a first flexure and a second flexure such that the first flexure and the second flexure permit only a linear deflection of the microarray, and
- wherein the microarray receptacle further comprises a force introduction structure connected indirectly or directly to a rear side of the microarray and/or the carrier surface and starting convexly therefrom.

* * * * *